United States Patent [19]

Siegel et al.

[11] Patent Number: 5,082,932
[45] Date of Patent: Jan. 21, 1992

[54] PROCESS FOR PREPARING SUBSTITUTED 1,2-NAPHTHOQUINONE-(2)-DIAZIDE-4-SULFONIC ACID ESTERS AND THEIR USE IN A RADIATION-SENSITIVE MIXTURE

[75] Inventors: Herbert Siegel, Hofheim/Taunus; Siegfried Scheler, Wiesbaden, both of Fed. Rep. of Germany

[73] Assignee: Hoechst Aktiengesellschaft, Frankfurt am Main, Fed. Rep. of Germany

[21] Appl. No.: 431,182

[22] Filed: Nov. 3, 1989

[30] Foreign Application Priority Data

Nov. 4, 1988 [DE] Fed. Rep. of Germany ....... 3837499

[51] Int. Cl.$^5$ .................. C07C 303/28; C07C 309/35
[52] U.S. Cl. .................................. 534/557; 534/556; 430/192; 430/193
[58] Field of Search ................................ 534/556, 557

[56] References Cited

U.S. PATENT DOCUMENTS

| | | | |
|---|---|---|---|
| 3,046,118 | 7/1962 | Schmidt | 534/557 X |
| 3,046,121 | 7/1962 | Schmidt | 534/557 X |
| 3,869,292 | 3/1975 | Peters | 96/115 R |
| 4,439,516 | 3/1984 | Cernigliaro et al. | 430/323 |
| 4,818,658 | 4/1989 | Martin et al. | 534/557 X |
| 4,873,169 | 10/1989 | Erdmann et al. | 430/192 |
| 4,931,549 | 6/1990 | Berner | 534/556 X |

FOREIGN PATENT DOCUMENTS

269846 7/1989 German Democratic Rep. ..... 534/557

OTHER PUBLICATIONS

Kosar, "Light-Sensitive Systems: Chemistry and Application of Nonsilver Halide Photographic Processes," John Wiley & Sons, Inc., New York, chapter 7.4, 1965, pp. 339-352.
Cava et al., "Condensed Cyclobutane Aromatic Systems. V. The Synthesis of Some α-Diazo-indanones: Ring Contraction in the Indane Series", Journal of the American Chemical Society (80), 1958, pp. 2257-2263.
Horner et al., "Über den Einfluss von Substituenten auf die Polarität der Carbonylgruppen in o-Benzochinonen," Chemische Berichte, 95, 1962, p. 1206.
Journal für Praktische Chemie, vol. 94, 1916, pp. 24-34.
Organic Syntheses, vol. 23, John Wiley & Sons, Inc., New York, 1943, pp. 42-45.
Organic Syntheses, vol. 21, John Wiley & Sons, Inc., New York, 1941, p. 91.
Knop et al., "Chemistry and Application of Phenolic Resins", Springer Verlag, New York, 1979, chapter 4, pp. 60-67.
Berichte der Deutschen Chemischen Gesellschaft, vol. 27, 1984, p. 3050.

Primary Examiner—Mary C. Lee
Assistant Examiner—Fiona T. Powers
Attorney, Agent, or Firm—Foley & Lardner

[57] ABSTRACT

The invention relates to a process for preparing 1,2-naphthoquinone-(2)-diazide-4-sulfonic acid esters of the general formula I

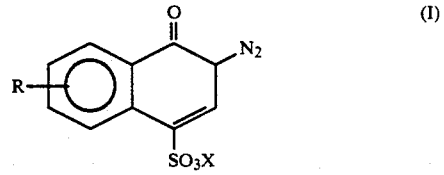

which are substituted in at least one of the positions 5, 6, 7 or 8 by R=halogen, alkoxy groups or alkoxycarbonyl groups and in which X denotes an aryl group. The process comprises steps in which
a) suitably substituted β-naphthol is nitrosated,
b) sulfonation with alkali hydrogensulfite and acid in position 4 and reduction are carried out,
c) the naphthalenesulfonic acid derivative is oxidized,
d) the 1,2-naphthoquinone-4-sulfonic acid formed is reacted with toluenesulfonohydrazide in an organic solvent at temperatures from 20° to 100° C.,
e) the naphthoquinonediazide compound is converted with chlorosulfonic acid or chlorosulfonic acid/thionyl chloride into the sulfonyl chloride, and f) the sulfonyl chloride is condensed with a phenolic component, a purification of the respective intermediate product by reprecipitation or recrystallization being unnecessary.

The process makes a simple technical procedure possible with good yield. The compounds prepared, in particular the 1,2-naphthoquinone-(2)-diazide-4-sulfonic acid esters substituted by 6-alkoxycarbonyl groups or by 7-alkoxy groups, are used as radiation-sensitive components in radiation-sensitive mixtures.

18 Claims, No Drawings

PROCESS FOR PREPARING SUBSTITUTED 1,2-NAPHTHOQUINONE-(2)-DIAZIDE-4-SULFONIC ACID ESTERS AND THEIR USE IN A RADIATION-SENSITIVE MIXTURE

BACKGROUND OF THE INVENTION

The invention relates to a process for preparing substituted 1,2-naphthoquinone-(2)-diazide-4-sulfonic acid esters starting from correspondingly substituted β-naphthol. The invention relates also to their use in a radiation-sensitive mixture with which corresponding recording materials can be prepared.

Naphthoquinonediazidesulfonic acids are used as photosensitive compounds for radiation-sensitive mixtures, such as for preparing photoresist mixtures or for preparing print forms (J. Kosar, "Light-Sensitive Systems", John Wiley & Sons, New York, chapter 7.4, 1965).

Their preparation starts from benzene- or naphthalenesulfonic acids which are substituted by hydroxyl groups and which are nitrosated with sodium nitrite in dilute aqueous acid, and the nitroso compound formed is isolated from the unreacted starting substances. The nitroso compound is then reduced to the corresponding amino compound which is separated off and resuspended in water in order to form the diazide compound at lower pH in the presence of sodium nitrite.

A disadvantage of this process is its multistage nature and the necessity of keeping the byproducts formed in aqueous solution and separating them from the main product formed in each case as a precipitate and purifying the product. Associated with this are, in addition to high production costs, low yield and insufficient product purity.

European Patent Application, Application number 88104043.0 discloses a process for preparing halogen-, nitro- or alkyl-substituted aryldiazidesulfonic acids in which the starting point is an arylsulfonic acid substituted by at least one hydroxyl group, and in which nitrosation and reduction of the resulting nitroso compound is carried out in the alkaline pH range. The amino compound is then converted into a sulfamate, the sulfamate derivative is mixed with a diazotizing agent and, after acidification, the aryldiazidesulfonic acid is obtained. In this process, the reaction product formed after each reaction step and suitable for further reaction remains in solution, but the final product is not free of isomeric compounds.

Nucleus-substituted 1,2-naphthoquinone-(2)-diazide-4-sulfonic acid esters are of interest for preparing photoresists. Their photosensitivity range is extended by the substituents.

To produce such photoresists, it is important that an economical process for preparing the photosensitive components is available.

SUMMARY OF THE INVENTION

Accordingly, it is an object of the present invention to provide a process for preparing a substituted 1,2-naphthoquinone-(2)-diazide-4-sulfonic acid ester which comprises simple process steps and gives a good yield.

In accomplishing the foregoing objectives, there has been provided, in accordance with one aspect of the present invention, a process for preparing a 1,2-naphthoquinone-(2)-diazide-4-sulfonic acid ester of the general formula I

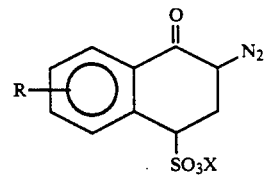

wherein R denotes a halogen, alkoxy or alkoxycarbonyl substituent in at least one of the positions 5, 6, 7 or 8, and wherein X denotes an aryl group, which comprises the steps of nitrosating a correspondingly substituted β-naphthol to form an o-quinone oxime; sulfonating the o-quinone oxime in position 4 with alkali hydrogen sulfite and acid and reducing the resultant compound to form a 1-amino-2-hydroxy-4-naphthalenesulfonic acid; oxidizing the 1-amino-2-hydroxy-4-naphthalenesulfonic acid to form an o-1,2-naphthoquinone-4-sulfonic acid; reacting the o-1,2-naphthoquinone-4-sulfonic acid with toluenesulfonohydrazide in an organic solvent at a temperature from about 20° to 100° C. to form a 1,2-naphthoquinone-(2)-diazide-4-sulfonicacid; reacting the 1,2-naphthoquinone-(2)-diazide-4-sulfonic acid with chlorosulfonic acid or a mixture of chlorosulfonic acid and thionyl chloride to form the corresponding sulfonyl chloride; and condensing the sulfonyl chloride with a phenolic compound.

In accordance with another aspect of the present invention, there is provided a process for preparing a 7-alkoxy-1,2-naphthoquinone-(2)-diazide-4-sulfonic acid ester of the general formula Ib

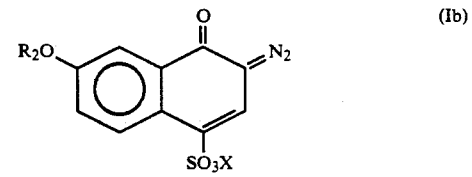

wherein $R_2$ denotes a branched or unbranched ($C_1$-$C_4$)alkyl group and wherein X denotes an aryl group, which comprises the steps of: reacting a 7-hydroxy-1,2-naphthoquinone-4-sulfonic acid with an alkylating agent to form the corresponding 7-alkoxy-1,2-naphthoquinone-4-sulfonic acid; and performing the diazotization, acid chloridation and esterification steps as previously described.

In accordance with another aspect of the present invention there is provided a radiation-sensitive compound produced by the above-recited process.

In accordance with a further aspect of the present invention, there is provided a radiation-sensitive mixture and a radiation-sensitive recording composition comprising a radiation-sensitive compound as described above.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

Preferably, as the starting substance for the process according to the invention, use is made of β-naphthols which are substituted by bromine, alkoxy groups containing 1 to 4 carbon atoms, or alkoxycarbonyl groups containing 2 to 5 carbon atoms.

In particular, β-naphthols which are substituted by bromine, methoxy groups or, in particular, by methoxy carbonyl groups, are suitable as commercially obtainable starting substance. The invention achieves the result that substituted 1,2-naphthoquinone-(2)-diazide-4-sulfonic acid derivatives are obtained with good yield in a simple manner. According to the invention, a purification of the respective intermediate product by reprecipitation or recrystallization is preferably unnecessary.

1,2-diazo ketones can be prepared from 1,2-diketones by reaction with toluenesulfonylhydrazide, as is described in J. Am. Chem. Soc. 80, 2257 (1958). It is furthermore known that this reaction may be used to prepare o-benzoquinonediazides. The experiments with unsymmetrically substituted o-benzoquinones published in Chem. Ber. 95, 1206 (1962) show that the reaction does indeed have a certain positional selectivity in the case of the compounds described there having electronically activating substituents. Nevertheless, as a rule, mixtures of isomers are formed, with the result that the method is unsuitable for preparing pure unsymmetrical o-benzoquinonediazides. In the case of 1,2-naphthoquinone derivatives which were unsymmetrical from the outset the formation of mixtures was also to be expected, in particular if these derivatives carry both activating and deactivating substituents. Because of the yield losses resulting therefrom, it was not possible to expect an economical process by this method.

Surprisingly, it has now been found that 1,2-naphthoquinone-(2)-diazide-4-sulfonic acids of the general formula Ia

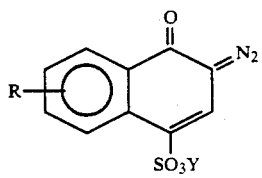

(Ia)

in which
R = halogen, $OR_1$ or $-CO-R_1$ with
$R_1$ = branched or unbranched ($C_1-C_4$)alkyl and
Y = H, $NH_4$ or alkali metal
are obtained in high yield and with excellent selectivity from the corresponding 1,2-naphthoquinone-4-sulfonic acids of the general formula II

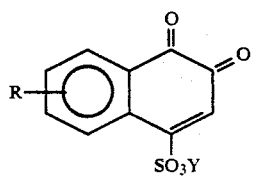

(II)

in which R and Y have the above-specified meaning, by reacting the latter at a temperature between 20° and 100° C. with toluenesulfonohydrazide in a polar solvent. It is especially surprising, and decisive for a technical usability of the process, that the likewise possible, but undesired naphthoquinonediazide isomer of the general formula III

(III)

in which R and Y have the above-specified meaning, is formed only in an insignificant proportion in relation to the isomer of the formula Ia, regardless of the nature of the substituent R.

To prepare the compounds of the formula Ia, the procedure is that either the o-quinone of the general formula II is taken in a polar organic solvent and toluenesulfonohydrazide is added at temperatures between 0° and 30° C., or, alternatively, the o-quinone of the formula II is taken together with the toluenesulfonohydrazide as a solid and a polar organic solvent is added at 0°-30° C. The reaction mixture, which exists, as a rule, as a suspension, is then heated to temperatures between 20° and 100° C., in which process the quinone goes into solution and the quinonediazide formed precipitates.

Particularly preferred are solvents such as alcohols since the naphthoquinonediazide of the formula Ia formed is only sparingly soluble in them and can thus be separated directly in high yield from the reaction mixture.

The reason why the process is very well suited for preparing the radiation-sensitive naphthoquinonediazides of the general formula Ia is, in particular, that isomers of the general formula III contained in small amounts do not interfere in the further processing to give the sulfonyl chlorides of the general formula IV

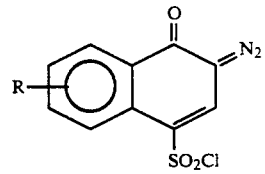

(IV)

in which R has the above-specified meaning. The processes standard for preparing such compounds produce the compounds of the general formula IV, for example, by reacting with chlorosulfonic acid or chlorosulfonic acid/thionyl chloride and subsequent precipitation with water. Whereas sulfonyl chlorides of the general formula IV can easily be isolated, the corresponding sulfonyl chloride of the general formula V

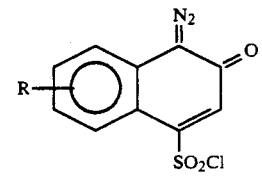

(V)

in which R has the above-specified meaning are so susceptible to hydrolysis that they are immediately decomposed to form the water-soluble sulfonic acids on precipitating the reaction mixture.

By combining the two steps, namely the reaction of 1,2-naphthoquinone-4-sulfonic acids of the general formula Ia with toluenesulfonohydrazide and the direct reaction of the crude product of this reaction to form the acid chloride and subsequent hydrolysis of the reaction mixture with water, isometrically pure sulfonyl chloride of the general formula IV is obtained directly.

The sulfonyl chloride of the general formula IV is a valuable starting material for the preparation of photosensitive sulfonic acid esters or can be converted by hydrolysis, for example with aqueous alkali, back into highly pure sulfonic acid of the general formula Ia.

The precursor of the general formula II is prepared in a known manner via three stages. In the first stage, a β-naphthol derivative of the general formula VI

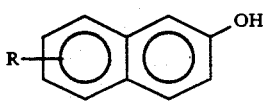
(VI)

in which R has the above-specified meaning, is nitrosated in accordance with the method described in J. prakt. Chem. 94, 24 (1916) by adding sodium nitrite solution to it at a temperature of 0°–5° C. in glacial acetic acid and continuing to stir at room temperature until all the starting material has reacted. The o-quinone oxime formed of the general formula VII

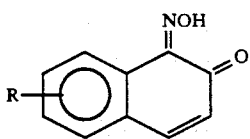
(VII)

in which R has the above-specified meaning is then precipitated with water, isolated and, if necessary, dried. In this procedure the crude product produced is so pure that it can be further processed without further purification, preferably as moist product which has been washed free of acid.

In the second stage, the o-quinone oxime of the general formula VII is first sulfonated with sodium hydrogensulfite in dilute solution and then reduced to the 1-amino-2-hydroxy-4-naphthalenesulfonic acid of the general formula VIII

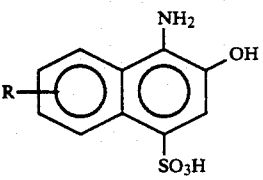
(VIII)

in which R has the above-specified meaning, by sulfurous acid liberated after acidification with sulfuric acid. The procedure corresponds partly to the process described in Organic Synthesis, Col. Vol. II, 42 (1943) in the preparation of 1-amino-2-hydroxy-4-naphthalenesulfonic acid. In this case it was found, however, that, in the case of the o-quinoneoximes of the general formula VII, it is more advantageous to extend the solution time of these compounds in the sulfonation with hydrogensulfite from a few minutes to a time of up to 24 hours or, alternatively, to raise the temperature to 30°–60° C. during the solution process. The advantage in this procedure is that less solution residue is obtained and consequently better yields are achieved. This is a substantial improvement of the method described, in particular in the case of the more sparingly soluble compounds with R=bromine. The reaction product of the general formula VIII is isolated by allowing it to crystallize out after acidifying, filtering off the crystals and, if necessary, drying. The quality of the crude products obtained is sufficient for them to be reacted further directly without further purification—preferably as a product which is moist with water.

In the third stage, the 1-amino-2-hydroxy-4-naphthalenesulfonic acid of the general formula VIII is oxidized to form the o-1,2-naphthoquinone-4-sulfonic acid of the general formula II

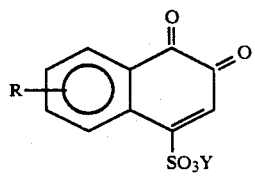
(II)

in which R and Y have the above-specified meaning, already described above, in accordance with the method specified in Organic Synthesis 21, 91 (1941) with an oxidizing agent such as, for example, nitric acid. Expediently, dilute nitric acid is employed so that the reaction mixture which is in the form of a suspension is capable of being stirred. The oxidation is preferably carried out at room temperature and the product formed is preferably isolated by salting out with ammonium chloride and subsequent filtration.

In addition, the intermediate product of the general formula II with $R=OR^1$, $R^1$ having the above-specified meaning, is reached in a manner known per se by preparing the o-quinone of the formula IX

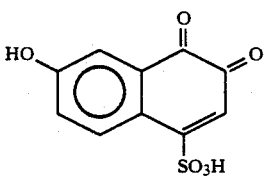
(IX)

in accordance with Chem. Ber. 27, 3050 (1894) and reacting the latter with an alkylating agent such as alkyl halide, dialkyl sulfate or alkyl toluenesulfonate.

The crude product so obtained contains, as a rule, small proportions of the corresponding 1,2-naphthoquinone-1-diazide-4-sulfonic acid of the general formula III (see above) which is formed under the reaction conditions in a side reaction from the starting material of the formula VIII with the nitrous acid formed during the oxidation. This impurity does not, however, interfere in the further reaction of the crude o-quinones of the formula II to form the o-quinone diazides of the formula I. As described above, it can easily be separated via the acid chloride hydrolysis at the stage of the acid chloride of the general formula IV. This has the advantage that a purification operation is also not necessary for the crude product at the synthesis stage explained here for the o-quinones of the general formula II and it can be processed further directly, preferably after drying.

The sulfonyl chloride of the formula IV is a valuable starting material for preparing radiation-sensitive esters of the general formula X according to the invention

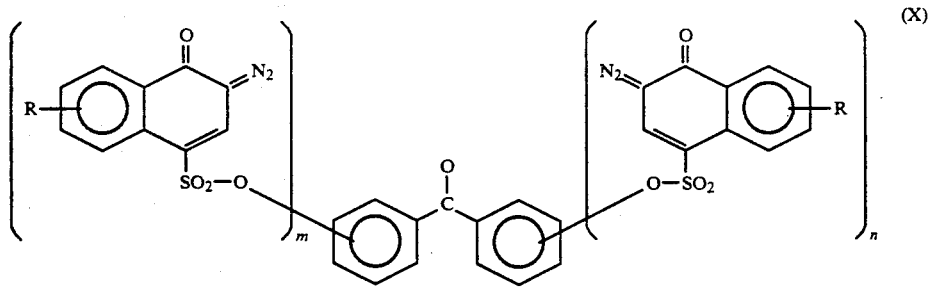

with m=1 to 3 and n=0 to 3.

The esters of the general formula X can be prepared by converting, for example, 6-bromo-1,2-naphthoquinone-(2)-diazide-4-sulfonic acid into the corresponding acid chloride and its reaction with a hydroxybenzophenone of the general formula XI

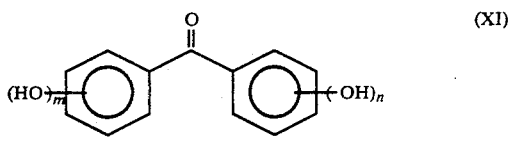

in which m and n have the above-specified meaning, by processes according to the prior art. In this case, however, the use of sterically hindered bases such as, for example, 1,4-diazabicyclo[2.2.2]octane (dabco) proves to be particularly advantageous and to go beyond the prior art. The esters are notable for high photosensitivity and are therefore suitable for preparing positive-working photoresists.

Other known phenols or their derivatives such as novolaks may serve as phenolic component.

The compounds prepared according to the invention, in particular the alkoxycarbonyl-1,2-naphthoquinone-(2)-diazide-4-sulfonic acid esters, such as the 6-alkoxycarbonyl-1,2-naphthoquinone-(2)-diazide-4-sulfonic acid ester, are intended as radiation-sensitive component in radiation-sensitive mixtures. The mixtures comprise the radiation-sensitive compound and a water-insoluble resinous binder which is soluble, or at least swellable, in aqueous alkaline solutions.

In combination with a coating base, the radiation-sensitive mixture applied forms a radiation-sensitive copying material such as a printing plate or a photoresist material.

Suitable binders are, for example, phenol novolak and cresol novolak and polyvinyl phenol resins.

The alkaline novolaks and polyvinyl phenol resins which may be used for the preparation of photosensitive mixtures are known. A process for preparing such novolaks is described in "Chemistry and Application of Phenolic Resins" by A. Knop and W. Scheib, Springer Verlag, N.Y., 1979, chapter 4. The use of polyvinyl phenols is known from U.S. Pat. Nos. 3,869,292 and 4,439,516.

To prepare the photosensitive mixtures according to the invention, the novolak or the polyvinylphenol and the radiation-sensitive compound are dissolved in a solvent. Suitable solvents for this purpose are, for example, glycol ethers such as, for example ethylene glycol monomethyl ether and ethylene glycol monoethyl ether, or alternatively, their acetates such as propylene glycol methyl ether acetate; esters such as, for example, ethyl acetate and butyl acetate; ketones such as, for example, methyl ethyl ketone, cyclopentanone and cyclohexanone; and also aromatic hydrocarbons such as, for example, toluene and xylene. Mixtures of these solvents may also be used.

Before being applied to a coating base, further additives such as, for example, colorants, dyestuffs, leveling agents, plasticizers, adhesion promoters, development accelerators, surfactants, for example nonionic surfactants, and cross-linking agents may be added to the radiation-sensitive mixture according to the invention.

In a preferred embodiment, the content of solid constituents in the radiation-sensitive mixture is about 15 to 99 percent by weight for the novolak or the polyvinylphenol, and about 1 to 85 percent by weight for the radiation-sensitive compound. In particular, the mixture contains the binder in a proportion of about 50 to 97 percent by weight, and very particularly preferably, of about 65 to 93 percent by weight, based on the weight of the solid constituents. The proportion of radiation-sensitive compound is, in particular, about 3 to 50 percent by weight and very particularly preferably, about 7 to 35 percent by weight, based on the weight of the solid constituents of the mixture.

According to the invention, a radiation-sensitive copying material is furthermore proposed which comprises the photosensitive mixture described above and a coating base.

The radiation-sensitive mixture may be applied to the coating base by one of the conventional methods such as immersion, spraying or spinning-on. In the case of spinning-on, the percentage proportion of solids in the resist solution may, for example, be adjusted in a manner such that, depending on the spinning-on equipment used in the individual case and on the time interval adopted for the spinning-on operation, a coating is produced in the desired thickness. Examples of suitable base materials are: silicon, aluminum or polymeric resins, silicon dioxide, doped silicon dioxide, silicon nitride, tantalum, copper, polycrystalline silicon (polysilicon) ceramic and aluminum/copper alloys.

The invention is explained in more detail by the following examples without being restricted thereto:

EXAMPLE 1

Ammonium 7-methoxy-1,2-naphthoquinone-(2)-diazide-4-sulfonate 35.6 g (0.125 mol) of ammonium 7-methoxy-1,2-naphthoquinone sulfonate and 23.5 g (0.126 mol) of toluenesulfonohydradize were suspended in 285 ml of methanol and the suspension was heated at 45° C. for one hour. Then the reaction mixture was cooled to 2° C. and the crystals filtered off by suction. 26.4 g (71%) of 7- methoxy-1-naphthoquinone-(2)-diazide-4-sulfonic acid was obtained as the ammonium salt.

Decomposition point: 151° C.

NMR (DMSO): 3.862 ppm (s; 3 H; CH$_3$); 7.301 ppm (dd; J$_1$=9,1 Hz; J$_2$=2.9 Hz; H on C-6); 7.567 ppm (d; J=2.9 Hz; H on C-8); 7.677 ppm (s; H on C-3); 8.461 ppm (d; J=9.1 Hz; H on C-5); 7.920 (t; J=51.3 Hz: NH$_4$+).

If crude o-quinone is used the product may also contain small amounts of the isomeric ammonium 7-methoxy-1,2-naphthoquinone-(1)-diazide-4-sulfonate as an impurity which originates from the precursor. During the reaction to form the acid chloride in an analogous manner to Example 3, this isomer is, however, completely removed as a consequence of hydrolysis, with the result that no further purification is necessary at the stage of the ammonium salt produced here.

Preparation of the precursors a) 1-Nitroso-7-methoxy-β-naphthol 110.2 g (0.633 mol) of 7-methoxy-β-naphthol were nitrosated in a mixture of 650 ml of glacial acetic acid and 65 ml of water at 0° C. in the course of two hours using a solution of 45.0 g (0.65 mol) of sodium nitrite in 340 ml of water. Stirring was continued for a further two hours and in this time the temperature of the reaction mixture was allowed to rise to 22° C. Then the volume was made up to 1.6 l with water and the precipitated product was filtered off by suction. After drying, 120.3 g (93.5%) of 1-nitroso-7-methoxy-β-naphthol were obtained.

Melting point: 122°–124° C.

NMR (DMSO): 3.855 ppm (s; CH$_3$); 6.276 ppm (d; J=9,8 Hz; 1H); 7.079 ppm (dd; J$_1$=2.6 Hz; J$_2$= 8.5 Hz; 1H); 7.515 ppm (d; J=8.5 Hz; 1H); 7.650 ppm (d; J=9.8 Hz; 1H); 8.222 ppm (broad s, 1H).

b) 1-Amino-2-hydroxy-7-methoxynaphthalene-4-sulfonic acid 168.4 g (1.62 mol) of sodium nitrogen sulfite were dissolved in 350 ml of water. 28 ml of 6N sodium hydroxide solution were added to this solution. It was then cooled to 10° C. and 120.1 g (0.59 mol) of crude 1-nitroso-7-methoxy-β-naphthol was stirred in. It was then diluted to a volume of 760 ml with water, during which process a temperature of 23° C. was established. Stirring was continued for 16 hours at room temperature and 9.5 g of insoluble residue was then filtered off. The filtrate was then made up to 1250 ml with water and 206.8 g (2.03 mol) of 96%-strength sulfuric acid were added, during which process the temperature rose by 10° C. The solution was allowed to stand for two days at room temperature and then the precipitated crystals were filtered off by suction. After drying, 108.5 g (68.4%) of 1-amino-2-hydroxy-7-methoxynaphthalene-4-sulfonic acid were obtained.

Melting point: 275° C. (decomposition)

NMR (DMSO): 3.886 ppm (s; CH$_3$); 4.029 ppm (broad s, 4H); 7.049 ppm (dd; J$_1$=2.3 Hz; J$_2$=9.3 Hz; 1H); 7.200 ppm (d; J=2.3 Hz; 1H); 7.653 ppm (2; 1H); 8.696 ppm (d; J=9.3 Hz; 1H).

c) Ammonium 7-methoxy-1,2-naphthoquinone-4-sulfonate 29.6 ml (0.556 mol) of 70.4%-strength nitric acid were diluted with 82 ml of water. 80.0 g (0.298 mol) of crude 1-amino-2-hydroxy-7-methoxynaphthalene-4-sulfonic acid were added while stirring to this solution of the oxidizing agent at not more than 30° C. in the course of one hour. Stirring was continued for 1 hour, followed by cooling to 10° C., and a solution of 17.6 g of ammonium chloride in 46 ml of water was added. The suspension was cooled to 0° C. for two hours and the product filtered off by suction. The crystals were rinsed first with 25 ml of saturated ammonium chloride solution and then with 40 ml of ethanol. After drying, 77.4 g (91.3%) of crude ammonium 7-methoxy-1,2-naphthoquinone-4-sulfonate were obtained.

Melting point: 210° C. (decomposition)

NMR (DMSO): 3.859 ppm (s; CH$_3$); 6.559 ppm (s, H on C-3); 7.274 ppm (dd; J$_1$=8.7 Hz; J$_2$=2.9 Hz: H on C-6); 7.411 ppm (d; J=2.9 Hz; H on C-8); 8.320 (d; J=8.7 Hz; H on C-5); 7.560 (t; J=51.1 Hz; NH$_4$+)

With this procedure, the product contains small amounts of ammonium 7-methoxy-1,2-naphthoquinone-(1)-diazide-4-sulfonate.

NMR (DMS0): 3.868 ppm (s; CH$_3$); 6.834 ppm (s, H on C-3); 6.894 ppm (dd; J$_1$=2.5 Hz; J$_2$=9.1 Hz; H on C-6); 7.020 ppm (d; J=2.5 Hz; H on C-8); 8.494 (d; J=9.1 Hz; H on C-5); 7.560 (t; J=51.1 Hz; NH$_4$+)

The purity of the crude product is, however, adequate for the further reactions.

EXAMPLE 2

Ammonium 6-bromo-1,2-naphthoquinone-(2)-diazide-4-sulfonate 71.0 g (0.213 mol) of ammonium 6-bromo-1,2-naphthoquinone-4-sulfonate and 40.2 g (0.216 mol) of toluenesulfonohydrazide were suspended in 475 ml of methanol and the suspension was heated for two hours at 44° C. Then the reaction mixture was cooled to 2° C. and the crystals were filtered off by suction.

62.1 g (84%) of ammonium 6-bromo-1,2-naphthoquinone-(2)-diazide-4-sulfonate were obtained. It was possible to obtain a further 11.7 g (16%) of the product from the mother liquor by evaporating down and digesting with ethyl acetate, with the result that the total yield of quinone diazide is virtually quantitative.

Decomposition point: 235° C.

NMR (DMSO): 7.638 ppm (dd; J$_1$=8.54 Hz; J$_2$=1.99 Hz; H on C-7); 7.905 ppm (s; H on C-3); 8.053 ppm (d; J=8.54 Hz; H on C-8); 8.691 ppm (d; J=1.99 Hz; H on C-5); 7.65 ppm (t; J=51.2 Hz; NH$_4$+)

If crude o-quinone is used, the ammonium salt obtained here may also contain small amounts of the isomeric quinonediazide. On reacting to form the acid chloride, the isomer is, however, completely removed as a consequence of hydrolysis, with the result that no further purification is necessary at the stage of the ammonium salt produced here.

Preparation of the precursors a) 1-Nitroso-6-bromo-β-naphthol 76.2 g (0.342 mol) of 6-bromo-β-naphthol were suspended in 385 ml of 90%-strength acetic acid and nitrosated for two hours at 4° C. with 28.5 g (0.413 mol) of sodium nitrite in 230 ml of water, and stirring was then continued for 23 h at room temperature. The suspension was then made up to twice its volume by filling up with water and the product formed was filtered off by suction. After drying, 83.8 g (97.3%) of crude 1-nitroso-6-bromo-β-naphthol whose purity is adequate for the further reaction was obtained.

Melting point: 144°–148° C.

NMR (DMSO): 6.48ppm(d; J=10.3 Hz; 1H);7.65 ppm (s; 1H);7.75ppm(d; J=2.1 Hz; 1H);7.68ppm (d; J=2.1 Hz; 1H); 8.65ppm(d; J=10.3 Hz; 1H)

b) 1-Amino-2-hydroxy-6-bromo-4-naphthalene sulfonic acid 84.8 g (0.337 mol) of crude 1-nitroso-6-bromo-$\beta$-naphthol were stirred into a solution of 97.5 g (0.939 mol) of sodium hydrogen sulfite and 4.0 g (0.1 mol) of sodium hydroxide solution in 376 ml of water at room temperature. The suspension was made up to 1350 ml with water and stirred for 24 hours at room temperature. Then 6.8 g (8% of the amount taken) of the solution residue were separated off by filtration. Then acidification was carried out with 119.4 g (1.17 mol) of 96%-strength sulfuric acid at no more than 30° C. and the product was crystallized out for 48 hours at room temperature. After filtration by suction and drying, 92.0 g (86%) of 1-amino-2-hydroxy-6-bromo-4-naphthalene sulfonic acid were obtained.

Melting point: 270° C. (decomposition)

NMR (DMSO): 7.73 ppm (d; J=1.5 Hz; 1H); 7.77 ppm (s; 1H); 7.86 ppm (s; 1H); 8.95 ppm (d; J=1.5 Hz; 1H); 5.42 ppm (broad s; 4H)

c) Ammonium 6-Bromo-1,2-naphthoquinone-4-sulfonate 80 g (0.252 mol) of crude 1-amino-2-hydroxy-6-bromo-4-naphthalene sulfonic acid were introduced into 105 ml of 24%-strength (0.478 mol) of nitric acid in portions while stirring at 22°–27° C. in the course of 80 minutes. A viscous suspension was formed and this was then cooled to 6° C. and 14.7 g (0.275 mol) of ammonium chloride in 38 ml of water were added to it. Stirring was continued for a further 30 minutes at 3° C. and the o-quinone formed was filtered off by suction. The crystals were washed consecutively with 40 ml of saturated ammonium chloride solution and 20 ml of ethanol. After drying, 71.4 g (85%) of crude ammonium 6-bromo-1,2-naphthoquinone-4-sulfonate were obtained.

Melting point: 225° C. (decomposition)

NMR (DMSO): 6.78 ppm (s; 1H); 7.83 ppm (d; J=1.7 Hz; 1H); 7.86 ppm (s; 1H); 8.56 ppm (d; J=1.7 Hz; 1H); 7,13 ppm (t; J=52.8 Hz; $NH_4^+$)

With this procedure, the product contains small amounts of ammonium 6-bromo-1,2-naphthoquinone-1-diazide-4-sulfonate.

NMR (DMSO): 7.008 ppm (s; H on C-3); 7.525 ppm (d; J=8.59 Hz; H on C-8); 7.684 ppm (dd; $J_1$=8.59 Hz; $J_2$=2.13 Hz; H on C-7); 8.728 ppm (d; J=2.13 HZ; H on C-5)

EXAMPLE 3

6-Bromo-1,2-naphthoquinone-(2)-diazide-4-sulfonyl chloride 60.0 g (0.174 mol) of ammonium 6-bromo-1,2-naphthoquinone-(2)-diazide-4-sulfonate were introduced into a mixture of 154 ml (2.31 mol) of chlorosulfonic acid and 48 ml (0.66 mol) of thionyl chloride in the course of 40 minutes. During this process the temperature rose from 19° to 40° C. The mixture was heated for a further 45 minutes at 60° C. and then cooled to room temperature. The reaction mixture was then poured onto ice water, the acid chloride formed being precipitated. The product was isolated on a sintered disk filter funnel and dried. 58.0 g (96%) of isomerically pure 6-bromo-1,2-naphthoquinone-(2)-diazide-4-sulfonyl chloride were obtained as a yellow solid.

Melting point: 182° C. (decomposition)

NMR (DMSO): 7.62 ppm (d; J=8.9 Hz; 1H); 8.06 ppm (s; H on C-3) 8.11 ppm (d., J=8.9 Hz; 1H); 8.73ppm(s; H on C-5)

EXAMPLE 4

2,3,4-Tris-(6-bromo-1,2-naphthoquinone-(2)-diazide-4-sulfonyloxy)benzophenone 28.0 g (0.081 mol) of 6-bromo-1,2-naphthoquinone-(2)-diazide-4-sulfonyl chloride and 6.2 g (0.027 mol) of 2,3,4-trihydroxybenzophenone were taken in 94 ml of acetonitrile. 8.8 g (0.087 mol) of N-methylmorpholine were added in the course of 30 minutes, in which process the starting material went into solution and the temperature rose from 17° C. to 30° C. Stirring was continued for a further 1.5 hours at room temperature and then the solution was acidified with 3.2 ml of glacial acetic acid. The reaction mixture was then stirred into 1 l of water. The precipitated product was filtered off by suction, washed with water until neutral and dried at 35° C. 30.6 g (97.5%) of triester were obtained as a yellow powder.

Melting point: 155° C. (decomposition)

$N_{found}$=6.8%, $N_{calc.}$=7.2%, $H_2O$=1.0%

EXAMPLE 5

Mixture of esters of 6-bromo-1,2-naphthoquinone-(2)-diazide-4-sulfonic acid and 1,2-naphthoquinone-(2)-diazide-5-sulfonic acid and 2,3,4-trihydroxybenzophenone 25.7 g (0.074 mol) of 6-bromo-1,2 naphthoquinone-(2)-diazide-4-sulfonyl chloride, 2.2 g (0.0082 mol) of 1,2-naphthoquinone-(2)-diazide-5-sulfonyl chloride and 6.3 g (0.027 mol) of 2,3,4-trihydroxybenzophenone were taken in 96 ml of acetonitrile. 9.0 g (0.089 mol) of N-methylmorpholine were added in the course of 20 minutes, during which process the temperature rose from 17° C. to 33° C. and the starting material went into solution. Stirring was continued for a further 1.5 hours and then the solution was acidified with 7 ml of 30%-strength hydrochloric acid. The reaction mixture was then stirred into 1 l of water. The precipitated product was filtered off by suction and dried at 35° C. 30.3 g (98.5%) of ester mixture was obtained as a yellow powder.

Melting point: 155° C. (decomposition)

$N_{found}$=7.4%, $N_{calc.}$=7.4%, $H_2O$=1.2%

EXAMPLE 6

2,3,4-Tris(6-methoxycarbonyl-1,2-naphthoquinone-(2)-diazide-4-sulfonyloxy)benzophenone Preparation of the precursors a) 1-Nitroso-6-methoxycarbonyl-$\beta$-naphthol 202.0 g (1.0 mol) of 6-methoxycarbonyl-$\beta$-naphthol were suspended in 1120 ml of 90%-strength acetic acid, nitrosated with 182 g (1.05 mol) of 40%-strength sodium nitrite solution at 0°–5° C. in the course of 2.5 hours and then stirring was continued at room temperature for 45 minutes. The suspension obtained was made up to 3 l with water, the solid was filtered off by suction and washed with water until neutral. After drying, 228.1 g (99.7%) of crude 1-nitroso-6-methoxycarbonyl-β-naphthol were obtained.

Melting point: 175° C. (decomposition)

NMR (DMSO): 3.90 ppm (s; CH$_3$); 6.50 ppm (d; J=9,9 Hz; 1H); 7.87 ppm (d; J=9.9 Hz; 1H); 8.04 ppm (dd; J$_1$=8.4 Hz; J$_2$=1.8 Hz; 1H); 8.16 ppm (d; J=1.8 Hz; 1H); 8.82 ppm (d; J=8.4 Hz; 1H)

b) Methyl 1-amino-2-hydroxy-4-sulfo-6-naphthalenecarboxylate 92.4 g (0.4 mol) of crude 1-nitroso-6-methoxycarbonyl-β-naphthol were added at room temperature to a solution of 360 g (1.11 mol) of 40%-strength aqueous sodium hydrogen sulfite and 4.4 g (0.11 mol) or sodium hydroxide in 1610 ml of water. The suspension was heated for 24 h at 40° C. and then 2.4 g; (2.6% of the amount taken) of residue were separated off. The clear solution was then acidified at 25° C. with 142 g (1.39 mol) of 36%-strength sulfuric acid and the product was crystallized out for 48 hours at room temperature. After filtration by suction and drying, 76.0 g (64%) of product is obtained.

Melting point: 280° C. (decomposition)

NMR (DMSO): 3.91 ppm (s; CH$_3$); 7.91 ppm (s; 1H); 7.90–8.00 ppm (m; 2H); 9.52 ppm (s; 1H)

c) Ammonium 6-methoxycarbonyl-1,2-naphthoquinone-4-sulfonate 90 g (0.3 mol) of crude methyl 1-methyl 1-amino-2-hydroxy-4-sulfo-6-naphthalenecarboxylate were introduced at 25°–30° C. into 116 ml of 24%-strength (0.57 mol) nitric acid in the course of 90 minutes. A viscous suspension was formed which was cooled to 5° C. and 17.5 g (0.325 mol) of ammonium chloride in 45 ml of water were added to it. Stirring was continued for a further hour at 5° C. and the o-quinone formed was filtered off by suction. The crystals were washed with 45 ml of ethanol. After drying, 75.0 g (79%) of crude 6-methoxycarbonyl-1,2-naphthoquinone-4-sulfonic acid were obtained as the ammonium salt.

Melting point: 212° C. (decomposition)

NMR (DMSO): 3.92 ppm (s; CH$_3$); 6.80 ppm (s; 1 H); 8.07–8.1 ppm (m; 2H); 9.02 ppm (s; 1H); 7.13 ppm (t; J=51.2 Hz; NH$_4$$^+$)

With this procedure, the product may also contain small amounts of ammonium 6-methoxycarbonyl-1,2-naphthoquinone(1)-diazide-4-sulfonate NMR (DMSO): 3.89 ppm (s; CH$_3$); 7.10 ppm (s; H on C-3); 7.65 ppm (d; J=8.5 Hz; H on C-8); 8.03 ppm (dd; J$_1$=8.5 Hz; J$_2$=1.8 Hz, H on C-7); 9.24 ppm (d, J=1.8 Hz; H on C-5)

d) Ammonium 6-methoxycarbonyl-1,2-naphthoquinone-(2)-diazide-4-sulfonate 69.8 g (0.223 mol) of ammonium 6-methoxycarbonyl-1,2-naphthoquinone-4-sulfonate and 42.3 g (0.227 mol) of toluenesulfonohydrazide were suspended in 450 ml of methanol and the suspension was heated at 40° C. for one hour. It was then cooled to 2° C. and the product was isolated on a sintered disk suction filter. After drying, 61.7 g (85.1%) of ammonium 6-methoxycarbonyl-1,2-naphthoquinone-(2)-diazide-4-sulfonate were obtained.

Melting point: 145° C. (decomposition)

NMR (DMSO): 3.93 ppm (s; CH$_3$); 7.97 ppm (s; H on C-3); 8.00 ppm (dd; J$_1$=8.3 Hz; J$_2$=1.7 Hz; H on C-7); 8.28 ppm (d; J=8.3 Hz; H on C-8); 9.20 ppm (d; J=1.7 Hz; H on C-5); 7.12 ppm (t; J=51.0 Hz; NH$_4$$^+$)

Any small quantities of the isomeric naphthoquinonediazide present are completely removed at the subsequent stage by acid chloride hydrolysis. Purification of the crude products obtained here is therefore unnecessary.

e) 6-Methoxycarbonyl-1,2-naphthoquinone diazide-4-sulfonyl chloride 60.0 g (0.185 mol) of ammonium 6-methoxycarbonyl-1,2-naphthoquinone-(2)-diazide-4-sulfonate were introduced into a mixture of 172 ml (2.58 mol) of chlorosulfonic acid and 54 ml (0.738 mol) of thionyl chloride in the course of 30 minutes. During this process the temperature of the mixture rose from 24° to 38° C. The mixture was heated for a further 1 hour at 50° C, cooled to room temperature and hydrolysed with ice water, in which process the acid chloride formed precipitated. After isolation and drying, 52.7 g (87.2%) of isomerically pure 6-methoxycarbonyl-1,2-naphthoquinone-(2)-diazide-4-sulfonyl chloride were obtained as a yellow solid.

Melting point: 180° C. (decomposition)

NMR (DMSO): 3.93 ppm (s; CH$_3$); 7.95 ppm (s; H on C-3); 7.98 ppm (dd; J$_1$=8.4 Hz; J$_2$=1.7 Hz; H on C-7); 8.27 ppm (d; J=8.4 Hz; H on C-8); 9.19 ppm (d; J=1.7 Hz; H on C-5)

f) 2,3,4-Tris(6-methoxycarbonyl-1,2-naphthoquinone-(2)-diazide-4-sulfonyloxy)benzophenone 15.0 g (0.046 mol) of 6-methoxycarbonyl-1,2-naphthoquinone-(2)-diazide-4-sulfonyl chloride and 3.52 g (0.0153 mol) of 2,3,4-trihydroxybenzophenone were taken in 240 ml of acetonitrile. 2.58 g (0.024 mole) of 1,4-diaza[2.2.2]bicyclooctane (dabco) were added at 25° C. under nitrogen. During this process the temperature rose to 29° C. and the starting material went into solution. After 30 minutes, 0.5 g (0.0044 mol) of dabco were again added and allowed to react for a further 3 hours. The reaction mixture was acidified with 10 ml of 30%-strength hydrochloric acid and then stirred into 720 ml of water. The precipitated product was filtered off by suction, washed with water until neutral and dried at 30° C. 14.9 g (88.4%) of triester were obtained as a yellow powder.

Melting point: 200° C. (decomposition)

N$_{found}$=7.11%, N$_{calc.}$=7.64% H$_2$O=1.6%

EXAMPLE 7 p-Cumylphenyl 6-methoxycarbonyl-1,2-naphthoquinone-(2)-diazide-4-sulfonate 11.3 g (0.0346 mol) of 6-methoxycarbonyl-1,2-naphthoquinone-(2)-diazide-4-sulfonyl chloride and 7.34 g (0.0346 mol) of p-cumylphenol were taken in 350 ml of acetonitrile. 4.54 g (0.045 mol) of N-methylmorpholine were added at 25° C. under nitrogen in the course of 10 minutes, during which process the starting material went into solution. After 3 hours, 0.92 g (0.009 mol) of N-methylmorpholine was added again, stirring was continued for 30 minutes and then 6 ml of 30%-strength hydrochloric acid were added. Then 1.035 l of water were added to the reaction mixture in the course of 45 minutes, the precipitated product was filtered off by suction, washed with water until neutral and dried at 30° C. 14.0 g (80.6%) of p-cumylphenyl ester was obtained as yellow crystals.

Melting point: 156° C. (decomposition)
$N_{found}=5.8\%$ $N_{calc.}=5.6\%$ $H_2O=0.3\%$

EXAMPLE 8

Silicon wafers are coated with a solution of
70.00 parts by weight (pbw) of cyclohexanone,
3.00 pbw of p-cumylphenyl 6-methoxycarbonyl-1,2-naphthoquinone-(2)-diazide-4-sulfonate and
27.00 pbw of cresol-formaldehyde novolak (melting range 122°–132° C. in accordance with DIN 53 181) on a resist spinner at a rotary speed of 5000 rev/min and then dried on a hot plate at a temperature of 110° C. for 60 s. The coating thickness is approx. 2.1 μm. Exposure is carried out with a projection exposure apparatus of the type FPA 1550 manufactured by Canon at a wavelength of 436 nm through a photomask which contains various line grids in a size range from 2.0 to 0.65 μm. The exposed wafers are developed by an immersion process using a developer of the type "AZ Developer 30" (manufactured by Hoechst AG) for 180 s, then rinsed with water and dried. A positive image of the photomask is obtained, lines and spaces having a width of 0.9 μm still being satisfactorily resolved at an exposure energy of 680 mJ/cm$^2$.

What is claimed is:

1. A process for preparing a 1,2-naphthoquinone-(2)-diazide-4-sulfonic acid ester of the formula

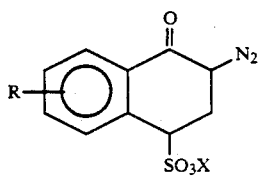

I wherein R denotes a halogen, alkoxy or alkoxycarbonyl substituent in at least one of the positions 5, 6, 7 or 8, and wherein X denotes an aryl group, which comprises the steps of:
   a) nitrosating a correspondingly substituted β-naphthol to form an o-quinone oxime;
   b) sulfonating said o-quinone oxime in position 4 with alkali hydrogen sulfite and acid and reducing the resultant compound to form a 1-amino-2-hydroxy-4-naphthalenesulfonic acid;
   c) oxidizing said 1-amino-2-hydroxy-4-naphthalenesulfonic acid to form an o-1,2-naphthoquinone-4-sulfonic acid;
   d) reacting said o-1,2-naphthoquinone-4-sulfonic acid with toluenesulfonohydrazide in an organic solvent at a temperature from about 20° to 100° C. to form a 1,2-naphthoquinone-(2)-diazide-4-sulfonic acid;
   e) reacting said 1,2-naphthoquinone-(2)-diazide-4-sulfonic acid with chlorosulfonic acid or a mixture of chlorosulfonic acid and thionyl chloride to form a 1,2-naphthoquinone-(2)-diazide-4-sulfonyl chloride; and
   f) condensing said sulfonyl chloride with a phenolic compound.

2. A process as claimed in claim 1, wherein said β-naphthol is substituted by bromine, alkoxy groups containing 1 to 4 carbon atoms, or alkoxycarbonyl groups containing 2 to 5 carbon atoms.

3. A process as claimed in claim 2, wherein said β-naphthol is substituted by at least one methoxy group or methoxycarbonyl group.

4. A process as claimed in claim 3, wherein said β-naphtol is substituted by at least one methoxycarbonyl group.

5. A process as claimed in claim 1, wherein a mixture of the isomers 1,2-naphthoquinone-(2)-diazide-4-sulfonic acid and 1,2-naphthoquinone-(1)-diazide-4-sulfonic acid is used to prepare said sulfonyl chloride and resultant isomers are separated by hydrolysis.

6. A process as claimed in claim 1, wherein a sterically hindered base is used for condensation with said phenolic component.

7. A process as claimed in claim 6, wherein said base is 1,4-diazabicyclo[2.2.2]octane.

8. A process as claimed in claim 1, wherein said phenolic compound is a hydroxybenzophenone derivative or a novolak.

9. A process for preparing a 7-alkoxy-1,2-naphthoquinone-(2)-diazide-4-sulfonic acid ester of the formula

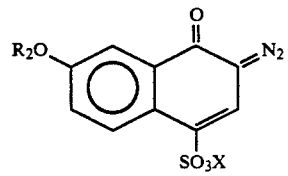

Ib wherein $R_2$ denotes a branched or unbranched ($C_1$–$C_4$) alkyl group and wherein X denotes an aryl group, which comprises the steps of:
   a) reacting a 7-hydroxy-1,2-naphthoquinone-4-sulfonic acid with an alkylating agent to form a corresponding 7-alkoxy-1,2-naphthoquinone-4-sulfonic acid;
   b) reacting said 7-alkoxy-1,2-naphthoquinone-4-sulfonic acid with toluenesulfonohydrazide in an organic solvent at a temperature from about 20° to 100° C. to form a 7-alkoxy-1,2-naphthoquinone-(2)-diazide-4-sulfonic acid;
   c) reacting said 7-alkoxy-1,2-naphthoquinone-(2)-diazide-4-sulfonic acid with chlorosulfonic acid or a mixture of chlorosulfonic acid and thionyl chloride to form a 1,2-naphthoquinone-(2)-diazide-4-sulfonyl chloride; and
   d) condensing said sulfonyl chloride with a phenolic compound.

10. A process as claimed in claim 9, wherein said alkylating agent is an alkyl halide, dialkyl sulfate or alkyl toluenesulfonate.

11. A process as claimed in claim 10, wherein said alkylating agent comprises a methyl group.

12. A process as claimed in claim 9, wherein a mixture of the isomers 1,2-naphthoquinone-(2)-diazide-4-sulfonic acid and 1,2-naphthoquinone-(1)-diazide-4-sulfonic acid is used to prepare said sulfonyl chloride and the resultant isomers are separated by hydrolysis.

13. A process as claimed in claim 9, wherein a sterically hindered base is used for condensation with said phenolic component.

14. A process as claimed in claim 13, wherein said base is 1,4-diazabicyclo[2.2.2]octane.

15. A process as claimed in claim 9, wherein said phenolic compound is a hydroxybenzophenone derivative or a novolak.

16. A 1,2-naphthoquinone-(2)-diazide-4-sulfonic acid ester produced by a process as claimed in claim 1.

17. A 1,2-naphthoquinone-(2)-diazide-4-sulfonic acid ester as claimed in claim 16, wherein said ester is a 6-alkoxycarbonyl-1,2-naphthoquinone-(2)-diazide-4-sulfonic acid ester.

18. A 7-alkoxy-1,2-naphthoquinone-(2)-diazide-4-sulfonic acid ester produced by a process as claimed in claim 9.

* * * * *